US005893842A

United States Patent [19]

Imbert

[11] Patent Number: 5,893,842

[45] Date of Patent: Apr. 13, 1999

[54] SYRINGE NEEDLE ISOLATION DEVICE

[75] Inventor: Claude Imbert, La Tronche, France

[73] Assignee: Becton, Dickinson and Company, Franklin Lakes, N.J.

[21] Appl. No.: 08/822,204

[22] Filed: Mar. 20, 1997

Related U.S. Application Data

[63] Continuation of application No. 08/304,976, Sep. 13, 1994, abandoned, which is a continuation of application No. 08/014,035, Feb. 5, 1993, abandoned.

[51] Int. Cl.$^6$ .................................................... A61M 5/50

[52] U.S. Cl. .......................... 604/110; 604/232; 604/236

[58] Field of Search .................................... 604/110, 187, 604/218, 232, 236, 237, 238, 240, 246, 249, 905; 128/917

[56] References Cited

U.S. PATENT DOCUMENTS

| | | | |
|---|---|---|---|
| 2,893,390 | of/1959 | Lockhart | 604/238 |
| 4,027,669 | 6/1977 | Johnston et al. . | |
| 4,387,879 | 6/1983 | Tauschinski | 604/247 X |
| 4,425,122 | 1/1984 | Cohen | 604/237 |
| 4,444,310 | 4/1984 | Odell | 206/366 |
| 4,460,357 | 7/1984 | Cohen | 604/238 |
| 4,919,655 | 4/1990 | Cline et al. | 604/110 |
| 4,929,230 | 5/1990 | Pfleger | 604/90 |
| 4,941,879 | 7/1990 | Butler et al. | 604/110 |
| 4,958,622 | 9/1990 | Selenke | 128/765 |
| 4,986,818 | 1/1991 | Imbert et al. | 604/192 |
| 5,000,735 | 3/1991 | Whelan | 604/110 |
| 5,034,002 | 7/1991 | Duränzampa et al. | 604/110 |
| 5,222,948 | 6/1993 | Austin et al. | 604/213 |
| 5,226,881 | 7/1993 | Pickhard | 604/110 |
| 5,308,330 | 5/1994 | Grimard | 604/110 |
| 5,353,837 | 10/1994 | Faust | 137/614.18 |

FOREIGN PATENT DOCUMENTS

| | | | |
|---|---|---|---|
| 0080379 | 6/1983 | European Pat. Off. | 604/905 |
| 0 344 956 A1 | 5/1989 | European Pat. Off. . | |
| 0 415 867 A1 | 3/1991 | European Pat. Off. . | |
| 0 453 667 A1 | 10/1991 | European Pat. Off. . | |
| 2 639 544 A1 | 11/1988 | France . | |
| 2632190 | 12/1989 | France | 604/110 |
| 9112038 | 8/1991 | WIPO | 604/110 |
| WO 91/120 | 8/1991 | WIPO . | |

OTHER PUBLICATIONS

English language abstract for FR 2 639544A1.

*Primary Examiner*—Michael Powell Buiz
*Assistant Examiner*—At Nguyen
*Attorney, Agent, or Firm*—Vincent A. Castiglione; John L. Voellmicke

[57] ABSTRACT

A syringe assembly having needle isolation features includes an elongate barrel having an open proximal end, a chamber for retaining fluid and a tip portion extending from a distal end of the barrel having a passageway therethrough include communication with the chamber. A valve housing extends outwardly from the tip portion of the barrel having a conduit therethrough in communication with the passageway. A needle cannula having a proximal end, a distal end and a lumen therethrough is provided. The proximal end of the needle is connected to the housing so that the lumen is in fluid communication with the conduit. The housing includes internal valve for allowing liquid under pressure in the chamber to flow distally through the conduit and the lumen while preventing unpressurized liquid in the chamber from flowing through the aperture. The internal valve includes a one-way valve structure for preventing liquid flow through the conduit in a proximal direction toward the chamber.

12 Claims, 7 Drawing Sheets

SYRINGE NEEDLE ISOLATION DEVICE

This application is a continuation of application Ser. No. 08/304,976, filed Sep. 13, 1994, abandoned, which is a continuation of application Ser. No. 08/014,035, filed Feb. 5, 1993, abandoned.

BACKGROUND OF THE INVENTION

1. Field of the Invention

The present invention relates to syringes and more particularly concerns syringe assemblies having needle isolation features.

2. Description of Related Information

Generally speaking, a hypodermic syringe consists of a cylindrical barrel, most commonly made of plastic or glass, with a distal end adapted to be connected to a hypodermic needle and a proximal end adapted to receive a stopper or plunger rod assembly. One of the purposes of the stopper is to provide a relatively air-tight seal between itself and the syringe barrel so that the movement of the stopper up and down the barrel will cause liquid, blood or other fluids to be drawn into or forced out of the syringe through the distal end.

A wide variety of injectable medications are prefilled in syringe barrel assemblies by pharmaceutical manufacturers, contract packagers, hospital pharmacies and the like. Medication contained in these syringes may sit for many weeks or months before administration of the medication to the patient. Under these circumstances, it is desirable to isolate the medication from the environment as thoroughly as possible. This task is more easily accomplished at the proximal end of the syringe where, a resilient rubber stopper can effectively seal the barrel. At the distal end of the syringe barrel, the problem of isolating the medication from the environment is more difficult to solve. In rigid barrel syringes, without hypodermic needles attached, it is common practice to seal the tip at the distal end of the syringe with elastomeric tip caps such as described in U.S. Pat. No. 4,444,310 where the tip cap is removed at the time of use and the hypodermic needle assembly is placed on the syringe tip. This type of tip cap works very well but requires the installation of a hypodermic needle at the time of use. Also, this type of tip cap does not discourage or prevent reuse of the syringe barrel.

Another method of sealing the distal end of the syringe, having a hypodermic needle attached, is through the use of a needle shield having a resilient element which seals the distal end of the needle as taught in U.S. Pat. No. 4,986,818. This method of sealing also works very well but may not be desirable where contact between the liquid medication and the needle cannula during storage is not desirable. Also, needle shields of this type do not prevent or discourage reuse of the syringe.

The art has recognized the use of hypodermic syringes for the efficient storage and delivery of liquid medication and has provided structure for sealing the distal end of the syringe barrel which has been proven over time to be efficacious. However, there is still a need for simple prefillable syringe device which combines all of the delivery and storage advantages of prior art hypodermic syringes but with the ability to store medication without contact with a needle cannula and to prevent refilling of the syringe through the syringe tip after the contents of the syringe have been expelled.

SUMMARY OF THE INVENTION

A syringe assembly of the present invention comprises an elongate barrel having an open proximal end, a distal end, a chamber for retaining fluid therebetween, and a tip portion extending from said distal end having a passageway therethrough communicating with the chamber. A stopper is slidably positioned in fluid-tight engagement inside the barrel. An elongate plunger rod projects proximally from the stopper and extends outwardly from the proximal end of the barrel. A valve housing extends outwardly from the tip portion of the barrel and includes a conduit therethrough in fluid communication with the passageway of the tip portion of the barrel. A needle cannula having a proximal end, a distal end and a lumen therethrough is connected to the housing so that the lumen is in fluid communication with the conduit. The housing includes internal valve structure for allowing fluid under pressure in the chamber to flow distally through the conduit and the lumen while preventing unpressurized liquid in the housing from flowing through the conduit. The internal valve structure also includes structure for preventing liquid flow through the conduit of the housing in a proximal direction toward the chamber.

In the preferred embodiment of this invention, the valve housing includes a cap portion having an open proximal end and a distal end connected to the needle cannula. The cap portion of the housing is secured to the tip portion of the barrel and a flexible valve is held within the cap between the tip of the barrel and the distal end of the cap portion. The valve interacts with the cap portion of the housing to allow liquid under pressure in the chamber to flow distally through the lumen of the needle cannula while preventing unpressurized liquid in the chamber from flowing through the conduit.

In another embodiment of the present invention the cap portion of the housing is integrally formed with the tip of the syringe barrel.

In another embodiment of the present invention the needle cannula is removably attached to the valve housing.

DETAILED DESCRIPTION

Figure 1:
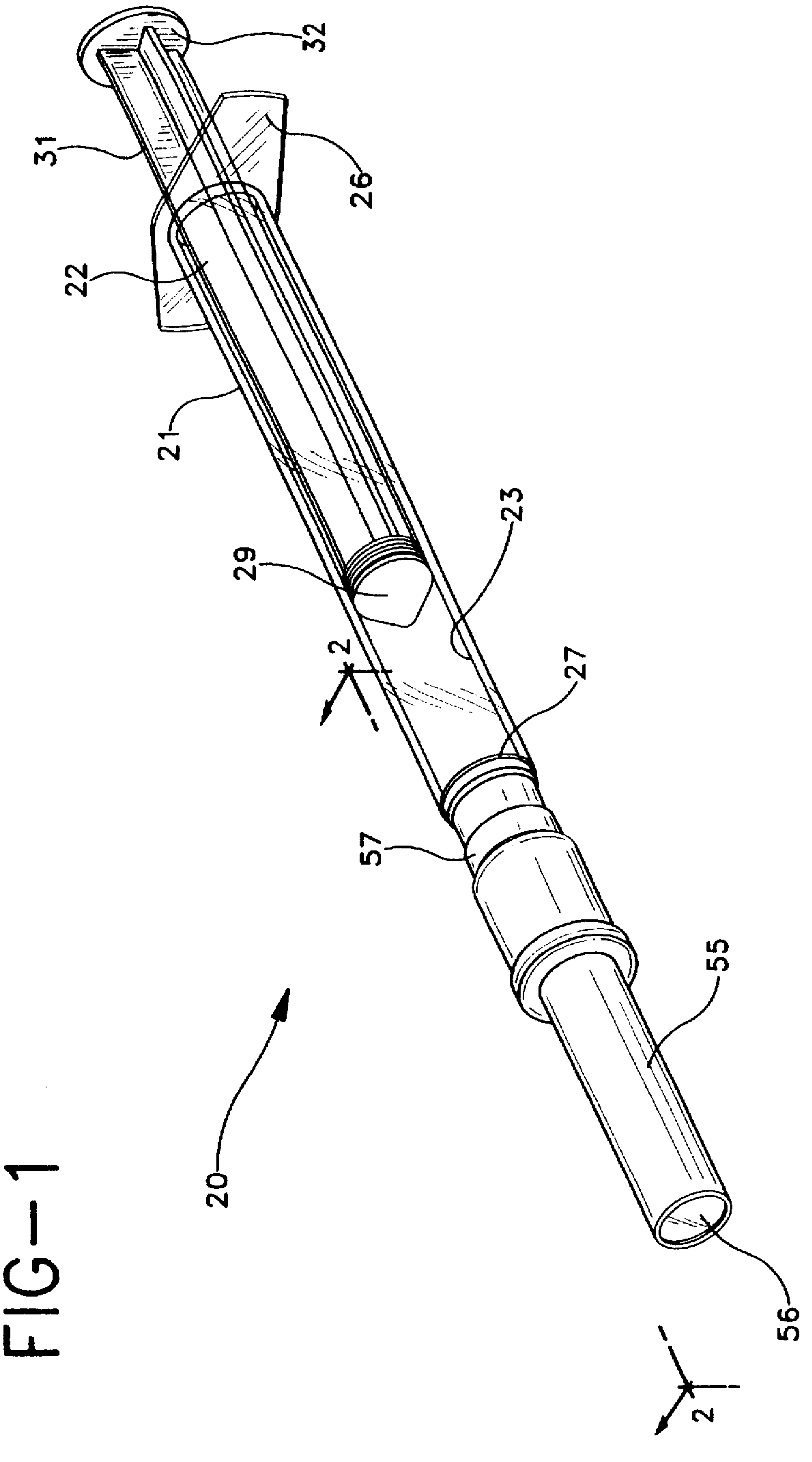
FIG. 1 is a perspective view of the syringe assembly of the present invention.
Figure 2:
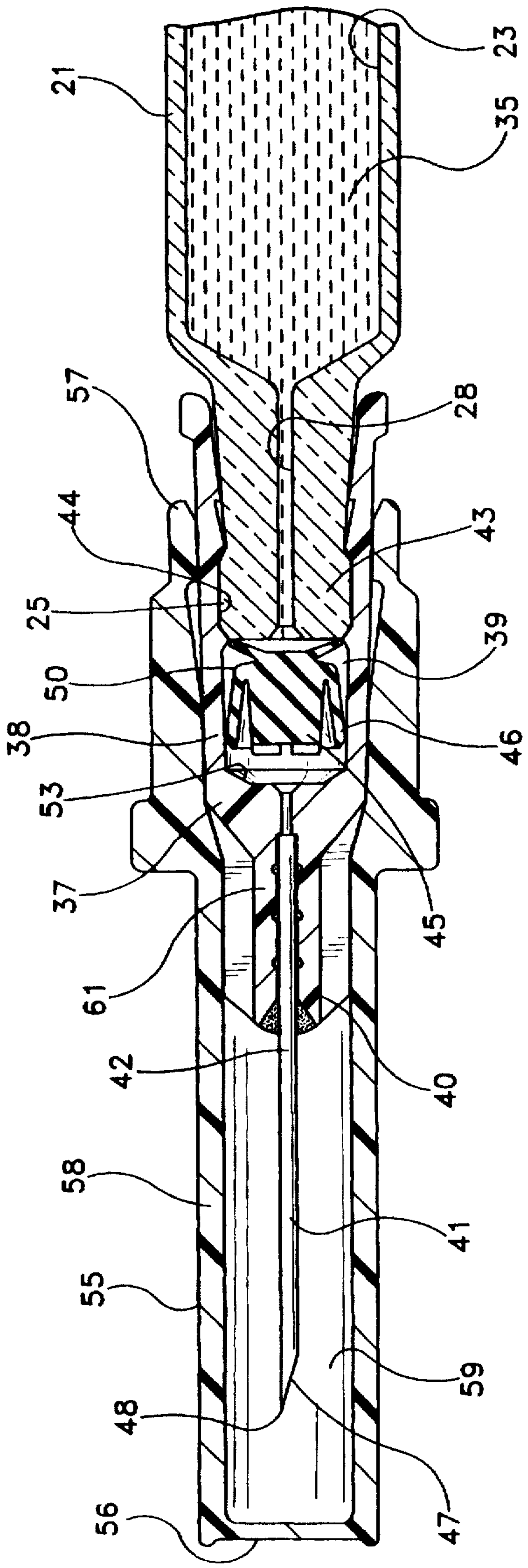
FIG. 2 is a cross-sectional view of the syringe assembly of FIG. 1 taken along line 2—2.

While this invention is satisfied by embodiments in many different forms, there is shown in the drawings and will herein be described in detail preferred embodiments of the invention with the understanding that the present disclosure is to be considered exemplary of the principles of the invention and is not intended to limit the invention to the embodiments illustrated. The scope of the invention will be measured by the appended claims and their equivalents.

Adverting to FIGS. 1–6, a syringe assembly 20 of the present invention comprises an elongate barrel 21 having an open proximal end 22, a chamber 23 for retaining liquid and a tip portion 25 extending from a distal end 27 of the barrel having a passageway 28 therethrough communicating with the chamber.

For the purposes of the description of the present invention, the term "distal end" is meant to refer to the end furthest from the person holding the syringe and closest to the needle whereas the term "proximal end" is meant to refer to the end closest to the holder of the syringe.

A stopper 29 is slidably positioned in fluid-tight engagement inside barrel 21 and is adopted to engage an elongate plunger rod 31 to facilitate its operation. The plunger rod projects proximally from the stopper and extends outwardly from the open proximal end of the barrel. The plunger rod is accessible outside of the proximal end of the barrel and is provided to move the stopper along the barrel to force liquid out of the chamber through the passageway. Specifically, the stopper is capable of moving liquid from chamber 23 through passageway 28 upon its movement toward distal end 27 of the barrel. In this embodiment, the stopper contains an internal thread (not shown) which engages an external thread (not shown) on the plunger rod. There are numerous other constructions that can be used to join a plunger rod and a stopper such as an interference or snap fit arrangement or through the use of adhesives. It is also possible to make a one-piece plunger stopper assembly such as by injection molding one or two materials in a mold cavity. The arrangement described hereinabove is exemplary of these many possibilities which are all within the purview of the present invention.

A disc-shaped plunger rod flange 32 is provided on the proximal end of the plunger rod. Flange 32 is a convenient structure for applying forces to move the plunger rod with respect to the barrel. The large surface area of the flange reduces the pressure on the fingers while delivering medication through the nasal sprayer.

A therapeutic liquid such as liquid medication 35 is contained within chamber 23. A valve housing 37 extends outwardly from the tip portion of the barrel and includes a conduit 39 therethrough in fluid communication with passageway 28. A needle cannula 41 is provided having a proximal end 42 and a distal end 47, and a lumen therethrough. In this embodiment distal end 47 includes a sharpened distal point 48. Proximal end 42 of the needle cannula is connected to the housing so that the lumen of the needle cannula is in fluid communication with conduit 39. In this embodiment, the needle cannula is fixedly attached to the housing.

The present invention includes means for preventing unpressurized liquid in the chamber from flowing through the needle cannula while allowing liquid under pressure in chamber 23 to flow distally through the conduit and needle cannula 41. This one-way valve feature allows the syringe assembly of the instant invention to be prefilled by a pharmaceutical manufacturer or in the hospital pharmacy and to be used at a future time or date. The one-way valve feature isolates the contents of the syringe from the environment and eliminates the need for other mechanisms to preclude flow through the distal end of the syringe assembly.

The needle isolation structure of this embodiment comprises two components, valve housing 37, having a cap-shaped portion 38 and a flexible valve 45. Cap portion 38 is secured to tip portion 25 of the barrel by virtue of an interference fit between enlarged portion 43 of tip 25 and interior surface 44 of the cap. In this embodiment the interference fit between the barrel, which is preferably made of glass, is a preferred way of joining these components. It should be noted that many materials are suitable for the barrel and for the cap and that numerous joining methods such as adhesive, heat sealing, and the like are all within the purview of the instant invention.

Figure 3:
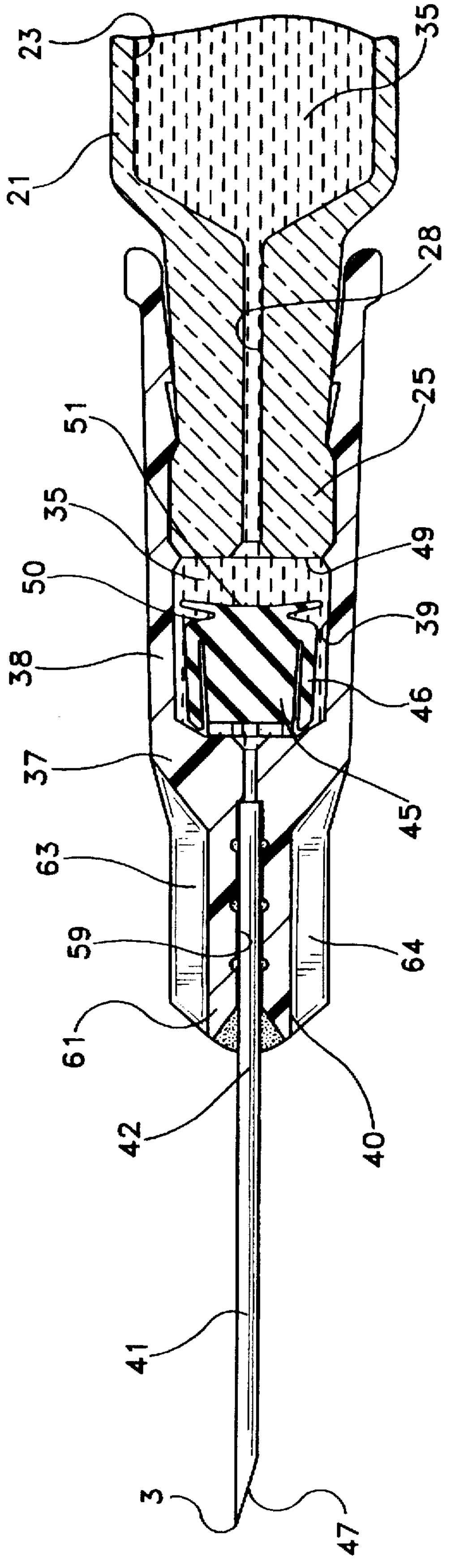
FIG. 3 illustrates the syringe assembly of FIG. 2 with liquid being forced through the valve and needle cannula.

Flexible valve 45 is contained within the cap portion between tip portion 25 of the barrel and distal end 53 of the cap portion. Flexible valve 45 interacts with cap portion 38 of housing 37 to allow liquid under pressure in the chamber to flow distally through needle cannula 41 preventing unpressurized liquid in the chamber from flowing through the aperture. The valve in this preferred embodiment is a skirt valve having a circumferential skirt 46 which will partially collapse under the force of pressurized liquid, as illustrated in FIG. 3, in the chamber to allow liquid to flow from the chambers through the spray aperture. The skirt collapses by moving away from the side wall of the cap allowing liquid to pass through the liquid pressure created gap between the skirt and the cap. Valve 45 also includes distal passageways 54 to assure that liquid flows freely through the chamber and into the lumen of needle.

An advantage of the syringe assembly of the instant invention is that a certain amount of pressure within chamber 23 is required before the valve will open. When the valve opens (i.e., the skirt collapses), the liquid must be pressurized such as by action of the plunger rod. Accordingly, the valve acts as a means for protecting the contents of the syringe during storage.

Tip portion 25 of the barrel includes a distal end surface 49 surrounding passageway 28. Flexible valve element 45 further includes proximal end 50 having a proximal end surface 51 which is shaped to contact distal end surface 49 of the tip in a fluid-tight arrangement before use of the syringe. In this configuration medication in the syringe barrel is not allowed to contact the housing so that any possible problems regarding the composition of the housing being compatible with the medication are eliminated. Accordingly, the valve element in the preferred embodiment isolates the medication in much the same manner as the prior art tip cap while still allowing the needle to be connected to the syringe during storage. This is an important feature of the present invention because the issue of drug compatibility can be restricted to the barrel material, the stopper material and the valve element material. The proximal end of the flexible valve is configured to include a circumferential resilient wall 52 which includes proximal end surface 51. At the time of use, pressurized fluid in the syringe barrel will cause resilient wall 52 to deflect distally allowing the fluid to pass around flexible valve element 45, as illustrated in FIG. 3.

In order to more clearly illustrate the invention, the distance between distal end surface 49 of the tip portion and distal end 53 of the cap is illustrated as being longer than the axial length of flexible valve 45. In actual practice it is preferred that this distance be approximately equal to the axial length of the flexible valve so that the vale does not move axially during use. With this construction proximal end surface 51 is held firmly against distal end surface 49 of the tip to form a fluid-tight seal around the tip in order to confine the contents of the syringe to the glass barrel. In other embodiments where it is not necessary to seal the tip of the syringe and it is allowable to have some of the medication enter the housing, the distance between distal end surface 49 of the tip portion and distal end 53 of the cap can be longer than the axial length of the flexible valve.

Another important feature and advantage of the preferred embodiment of the present invention over the prior art is that it cannot be refilled after use. Accordingly, this invention protects the user from potential infection, contamination or injury caused by refilling, using improper procedures, the wrong drug or in a non-sterile or contaminated environment. The single-use feature or means of the preferred syringe protects the patient by now allowing additional medication to be drawn into barrel chamber 23 through passageway 28 by placing the needle cannula in fluid communication with a liquid medication and pulling the plunger in a proximal direction with respect to the barrel to create a sub-atmospheric pressure in the chamber. This method, the most common method of filling a hypodermic syringe, cannot be practiced with the preferred embodiment of the instant invention because flexible valve resists liquid flow in a proximal direction. Flow in the proximal direction is resisted by skirt 46 of flexible valve 45 which expands against the walls of conduit 39 when liquid attempts to move proximally. Also, pressure differentials which tend to force liquid in a proximal direction will force the valve against distal end surface 49 of tip portion 25. The valve may also be designed to include an appropriately sized central projection (not shown) so that it will occlude or block passageway 28 when it is subjected to forces in a proximal direction.

The syringe assembly further includes a needle shield 55 having a closed distal end 56, an open proximal end 57 and a side wall 58 therebetween describing a needle receiving cavity 59. The needle shield is removably attached to the housing for protecting the needle before use. In this preferred embodiment, the needle shield frictionally engages the outside surface of the housing to hold it in its position until it is removed at the time of use of the syringe assembly.

The syringe of the present invention is intended to be originally filled from the open proximal end of the barrel. The stopper is then inserted using an assembly tool which will allow air to escape while the stopper is being inserted into the barrel. Preferably the stopper can be inserted while the syringe and medication are in an evacuated chamber so that little or no air is trapped in the chamber when the stopper is inserted. A syringe so filled by a pharmaceutical manufacturer or other entity remote from the ultimate user is referred to as a prefilled syringe.

Figure 4:
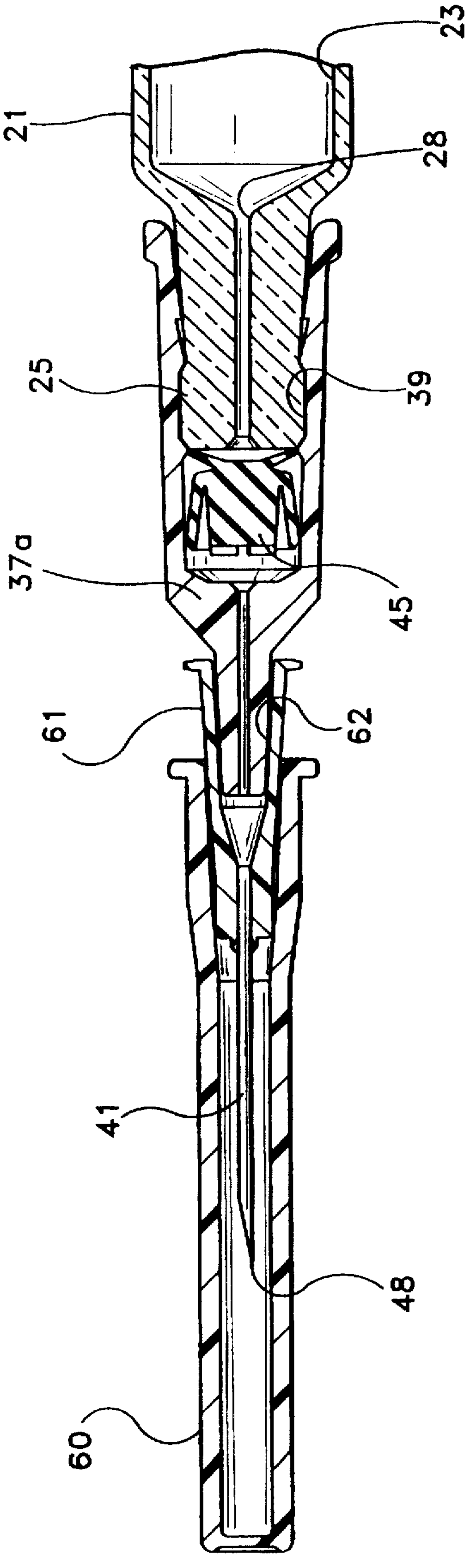
FIG. 4 illustrates an alternative embodiment of the syringe assembly of FIG. 2 having a removable needle cannula.
Figure 5:
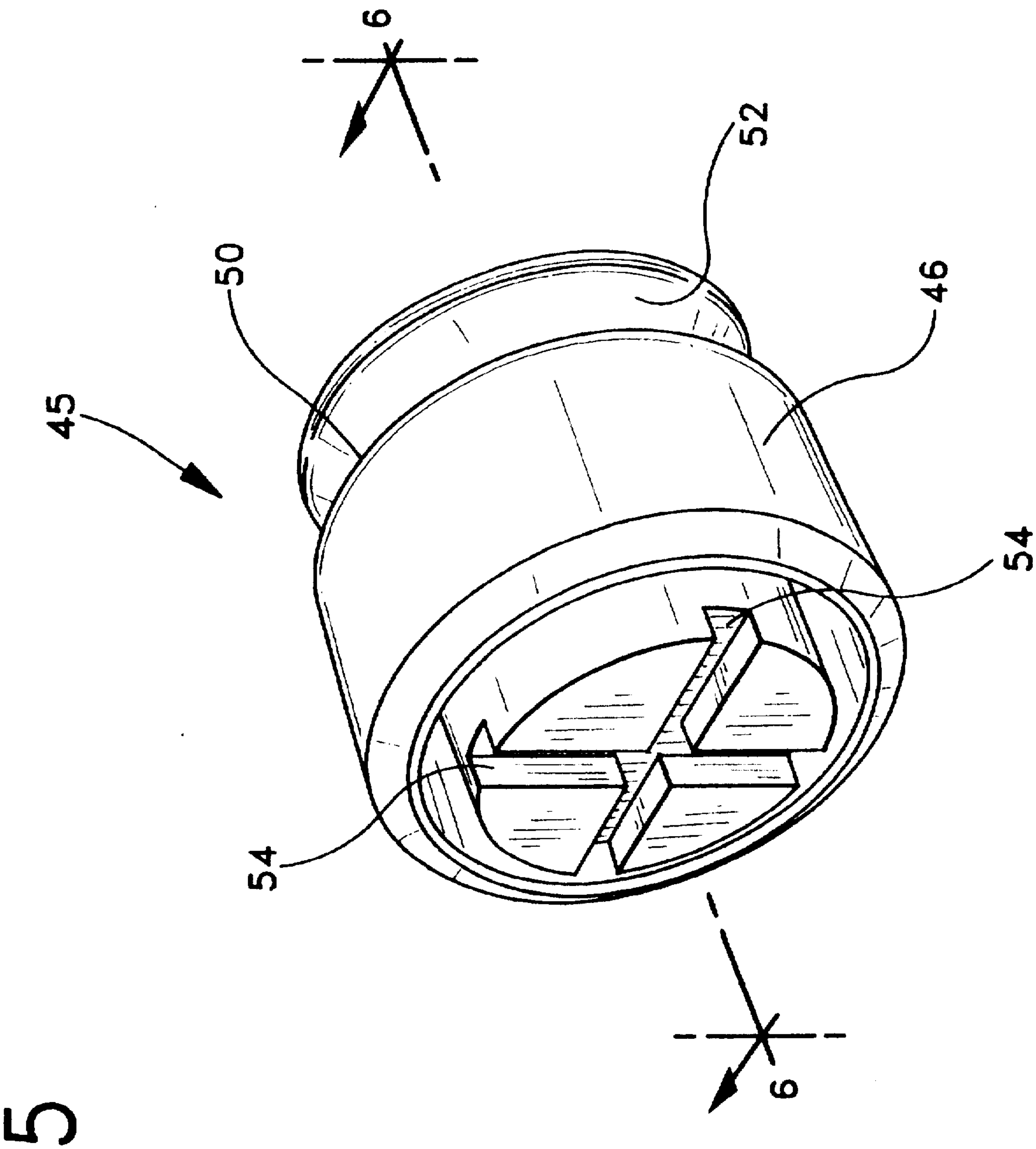
FIG. 5 is a perspective view of the valve element used in the syringe assembly of FIG. 1.
Figure 6:
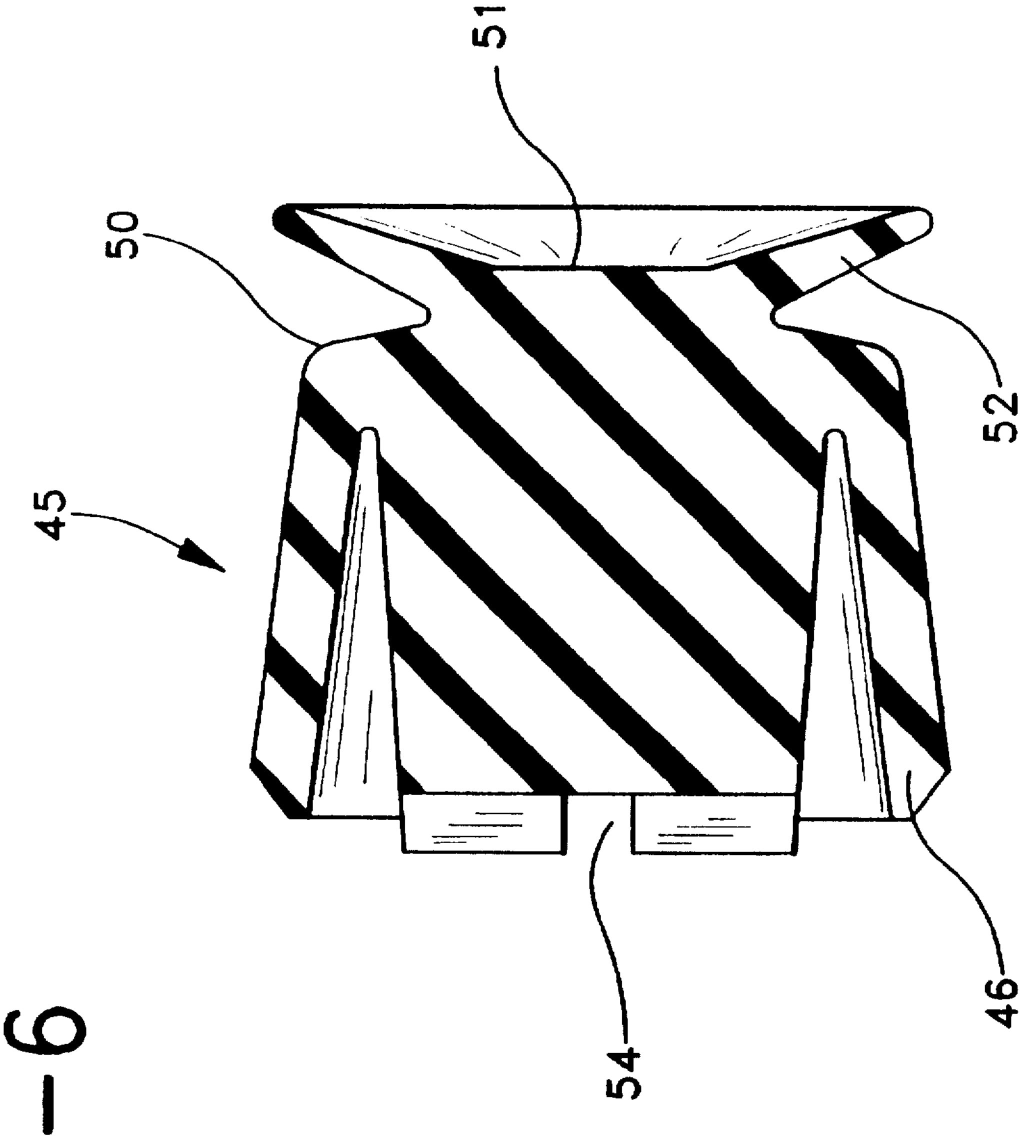
FIG. 6 is a side elevation view of the valve element of FIG. 5 taken along line 6—6.

FIG. 4 illustrates an alternative structure for the connection between the needle cannula and the housing. It is within the purview of the present invention to have a needle cannula which is fixedly attached to the housing or removably connected to the housing. In FIG. 4 needle cannula **41*a* is fixedly attached to needle hub 61 to form a needle assembly which is known and commercially available. Needle hub 61 includes interior frusto-conically shaped surface 62 which frictionally engages exterior surface of housing 37*a*. This variation in structure allows the prefiller or manufacturer the option to provide various needle sizes depending on the medication being filled into the syringe barrel. With a removable needle assembly a needle shield 60 which engages the needle hub is preferable. In all other respects the syringe assembly illustrated in FIG. 4 functions and is structured in the same way as the syringe assembly illustrated in FIGS. 1–3 using the valve element illustrated in FIGS. 5–6**.

Figure 7:
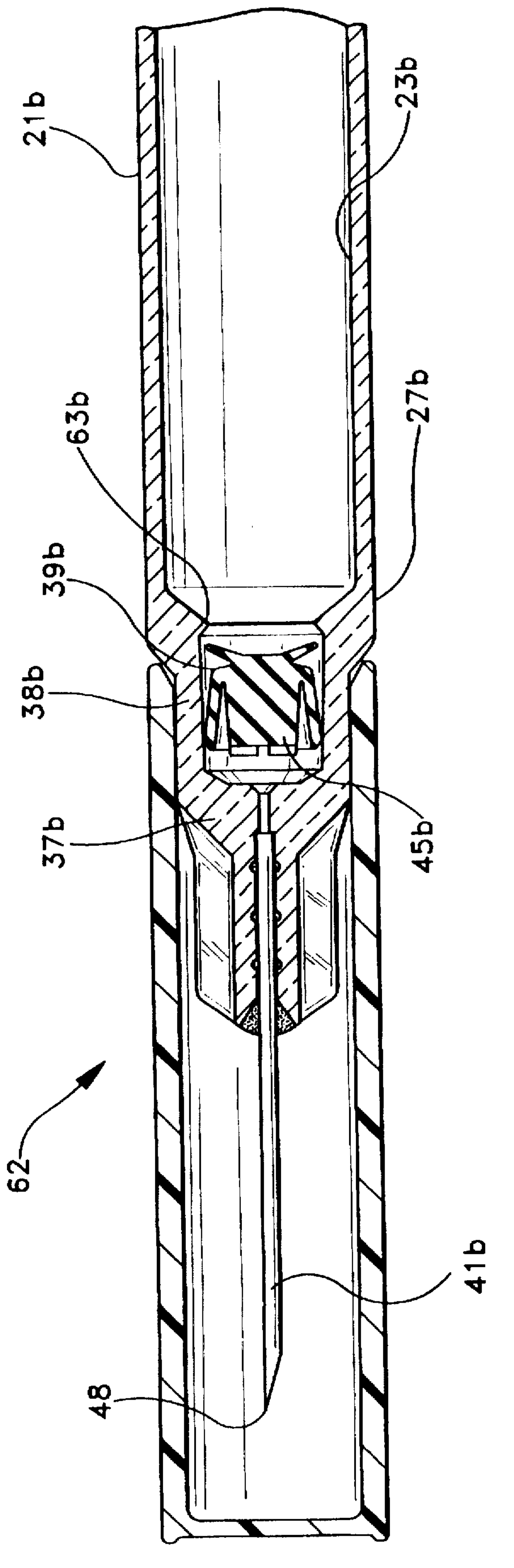
FIG. 7 is a side elevational view, cross-sectional, of an alternative embodiment of the syringe assembly of the present invention.

Referring now to FIG. 7 wherein an alternative syringe assembly 65 is illustrated. In this embodiment the structure of the syringe assembly is substantially similar to the syringe assembly of the embodiments of FIGS. 1–6. Accordingly, substantially similar components that perform substantially similar functions will be numbered identically to the components in the embodiment of FIGS. 1–6 except a suffix "b" will be used to identify those components in FIG. 7.

In this alternative embodiment, syringe assembly 62 includes elongate barrel **21*b* having an open proximal end, a chamber 23*b* for retaining fluid and a distal end 27*b***.

In the embodiment of FIGS. 1–6 valve housing 37 includes cap portion 38 and a flexible valve 45. In this alternative embodiment of FIG. 7 valve housing **37*b* includes a cap 38*b* and flexible valve 45*b*. Accordingly, in this embodiment, cap 38*b* is integrally formed with barrel 21*b*** to produce an integral cap-tip structure in lieu of the separate barrel tip and cap structure of the preferred embodiment.

The distal end of housing **37*b* includes cannula 41*b* in fluid communication with conduit 39*b*. Internally positioned flexible valve 45*b*** allows liquid under pressure in the chamber to flow distally through the conduit and through the aperture while preventing unpressurized liquid in the chamber from flowing through the aperture. In this embodiment, the tip portion and the cap portion, as previously indicated, are all one-piece so that the barrel and the flexible valve comprise a two-component assembly.

This embodiment includes means for holding the flexible valve in the cap portion so that subatmospheric pressure in chamber **23*b* will not pull the valve back in the chamber. In this embodiment, inwardly projecting ledge 63*b*** is formed inside the passageway to prevent withdrawal of the flexible valve from its distal position. Different means may be employed to position the valve depending on the materials and the valve design employed.

In use the syringe assembly of the alternative embodiment of FIG. 7 functions in the same manner to deliver a therapeutic liquid as does the embodiment of the syringe assembly of FIGS. 1–6.

The barrel of the present invention may be constructed of a wide variety of rigid materials such as metals, plastics and ceramics. Glass is preferred due to its long moisture vapor transmission rate and compatibility with many medication formulations.

A wide variety of rigid materials are suitable for formation of the plunger rod and valve housing. These materials include metals or plastic with injection molded plastic being preferred.

A wide variety of materials such as natural rubber, synthetic rubber, thermoplastic elastomers, thermoplastic and thermosets are suitable for forming the flexible valve with thermoplastic and thermoplastic elastomers being preferred.

A wide variety of materials such as natural rubber, synthetic rubber and thermoplastic elastomers are suitable for forming a stopper with natural rubber and butyl rubber being preferred.

Thus the present invention provides a straight-forward, reliable, easily fabricated syringe assembly which provides simplicity of design with the ability to store therapeutic liquids in a syringe having its needle cannula connected during storage.

The present invention also isolates liquid medication without use of barriers that must be pierced or punctured therefore eliminating the possibility of particulate contamination and the complexity of providing additional structure to pierce the barrier.

What is claimed is:

1. A prefilled syringe assembly comprising:

an elongate barrel having an open proximal end, a distal end, a chamber for retaining a quantity of fluid therebetween and a tip portion extending from said distal end having a passageway therethrough communicating with said chamber;

a stopper slidably positioned in fluid-tight engagement inside said barrel;

an elongate plunger rod for applying a distally-directed pressure on the quantity of fluid retained within said chamber, said plunger rod projecting proximally from said stopper and extending outwardly from said proximal end of said barrel;

a housing extending outwardly from said tip portion of said barrel having a conduit therethrough in fluid communication with said passageway;

a needle cannula having a proximal end, a distal end and a lumen therethrough, said proximal end of said needle connected to said housing so that said lumen is in fluid communication with said conduit;

said housing including an internal valve assembly for allowing liquid under pressure in said chamber to flow distally through said conduit and said lumen while preventing unpressurized liquid in said chamber from flowing through said conduit and through said lumen;

said internal valve assembly including a one-way valve having a proximal end surface disposed in fluid-tight contact with the tip portion of the barrel when the quantity of fluid in said chamber is not subjected to said distally-directed pressure and which is spaced away from the tip portion of the barrel when the fluid retained in the chamber is subjected to said distally directed pressure, said one-way valve thus configured to permit liquid flow through said passageway only in a distal direction away from said chamber and to preclude liquid flow through said passageway in a proximal direction;

wherein a quantity of liquid held in said chamber will be isolated against inadvertent entry of liquid in a proximal direction through said lumen.

2. The syringe assembly of claim 1 wherein said valve assembly includes means for preventing unpressurized liquid from contacting said conduit of said housing.

3. The prefilled syringe assembly of claim 1 wherein said housing includes: a cap portion having an open proximal end and a distal end connected to said needle cannula, said cap portion being secured to said tip portion; and said one-way valve comprising a flexible valve within said cap portion, between said tip portion and said distal end of said cap portion, said flexible valve interacting with said cap portion to allow fluid under said distally-directed pressure in said chamber to flow distally through said lumen of said needle cannula, while preventing fluid not subject to said distally-directed pressure in said chamber from flowing through said passageway.

4. The prefilled syringe assembly of claim 3 wherein said flexible valve is made of material selected from the group consisting of: thermoplastic, thermoplastic elastomers, natural rubber, synthetic rubber and thermosetting plastic.

5. The prefilled syringe assembly of claim 1 wherein said one-way valve comprises a skirt valve oriented so that said skirt valve will partially collapse under said distally-directed pressure applied to the fluid in said chamber to allow fluid to flow only in a distal direction from said chamber through said passageway.

6. The prefilled syringe assembly of claim 5 wherein said tip portion of said barrel includes a distal end surface surrounding said passageway and said skirt valve includes said proximal end surface in fluid-tight contact with said distal end surface of said tip when the fluid retained in the chamber is not subject to said distally-directed pressure.

7. The prefilled syringe assembly of claim 1 wherein said housing includes: a cap portion having a distal end connected to said needle cannula, said cap portion being integrally formed with said tip portion of said barrel; said one-way valve comprising a flexible valve disposed within said cap; and means for holding said one-way valve in said cap.

8. The prefilled syringe assembly of claim 1 wherein said needle cannula is removably connected to said housing.

9. The prefilled syringe assembly of claim 1 further including a needle hub between said needle cannula and said housing, said needle cannula being fixedly attached to said hub to form a unitary assembly and said hub being removably connected to said housing.

10. The prefilled syringe assembly of claim 9 further including a needle shield having a closed distal end, an open proximal end and a side wall therebetween describing a needle receiving cavity, said needle shield being removably attached to said housing for protecting the needle before use.

11. The prefilled syringe assembly of claim 1 wherein said liquid is a therapeutic liquid.

12. The prefilled syringe assembly of claim 1 further including a needle shield having a closed distal end, an open proximal end and a side wall therebetween describing a needle receiving cavity, said needle shield being removably attached to said housing for protecting the needle before use.

* * * * *